United States Patent
Rudolph et al.

(10) Patent No.: US 9,072,784 B2
(45) Date of Patent: Jul. 7, 2015

(54) METHOD FOR STABILISING PHARMACEUTICAL ADMINISTRATION FORMS COMPRISING MICROORGANISMS

(75) Inventors: Markus Rudolph, Vich (CH); Stefan Henke, Kirchen (DE); Iris Manneck, Luins (CH); Holger Peitz, Ginsheim (DE); Andrea Christ, Heidelberg (DE)

(73) Assignee: Merck Patent GmbH, Darmstadt (DE)

( * ) Notice: Subject to any disclaimer, the term of this patent is extended or adjusted under 35 U.S.C. 154(b) by 2075 days.

(21) Appl. No.: 12/088,479

(22) PCT Filed: Aug. 30, 2006

(86) PCT No.: PCT/EP2006/008468
§ 371 (c)(1),
(2), (4) Date: Mar. 28, 2008

(87) PCT Pub. No.: WO2007/036278
PCT Pub. Date: Apr. 5, 2007

(65) Prior Publication Data
US 2008/0219961 A1    Sep. 11, 2008

(30) Foreign Application Priority Data
Sep. 29, 2005   (EP) .................................. 05021254

(51) Int. Cl.
| A61K 47/26 | (2006.01) |
| A61K 9/16 | (2006.01) |
| A61K 9/20 | (2006.01) |
| A61K 9/24 | (2006.01) |
| A61K 9/48 | (2006.01) |
| B65D 81/26 | (2006.01) |

(52) U.S. Cl.
CPC ................ *A61K 47/26* (2013.01); *A61K 9/1658* (2013.01); *A61K 9/2018* (2013.01); *A61K 9/209* (2013.01); *A61K 9/4858* (2013.01); *A61K 9/4866* (2013.01); *B65D 81/26* (2013.01)

(58) Field of Classification Search
CPC ........... A61K 31/4155; A61K 2300/00; A61K 31/4439; A61K 31/506; A61K 31/444; A61K 45/06; A61K 31/497; A61K 31/522; A61K 31/5365; A61K 31/427; A61K 31/513; A61K 31/519; A61K 31/52; A61K 47/26; A61K 9/1658; B01L 2300/0851; B01L 2300/021; B01L 2300/0645; B01L 2300/0829; B01L 3/5085; B01L 2300/12; B01L 9/50; B01L 3/50855; B01L 2200/023; B01L 2200/025; B01L 2200/0673; B01L 2200/0689; B01L 2300/041
See application file for complete search history.

(56) References Cited

U.S. PATENT DOCUMENTS

| 4,667,814 A | 5/1987 | Wakamatsu |
| 6,254,886 B1 * | 7/2001 | Fusca et al. ................... 424/464 |

FOREIGN PATENT DOCUMENTS

| EP | 1072258 A | | 1/2001 |
| WO | WO9732663 | * | 9/1997 |
| WO | WO 98/41103 A | | 9/1998 |
| WO | WO 2005/063200 A | | 7/2005 |

OTHER PUBLICATIONS

Anonymus: "Desiccant film packages nearing market" in-pharmatechnologist.com, [Online[ Aug. 24, 2005, XP002437467.

* cited by examiner

*Primary Examiner* — Debbie K Ware
(74) *Attorney, Agent, or Firm* — Millen, White, Zelano, Branigan, P.C.

(57) ABSTRACT

The invention relates to a method for stabilizing solid pharmaceutical administration forms which comprises at least one species of microorganism, and to a pack comprising packaging and a solid pharmaceutical administration form which comprises at least one species of microorganism.

16 Claims, No Drawings

METHOD FOR STABILISING PHARMACEUTICAL ADMINISTRATION FORMS COMPRISING MICROORGANISMS

The invention relates to a method for stabilising solid pharmaceutical administration forms which comprises at least one species of microorganism, and to a pack comprising packaging and a solid pharmaceutical administration form which comprises at least one species of microorganism.

Microorganisms are frequently present in solid pharmaceutical administration forms, where the latter can be administered orally, vaginally or anally. Thus, for example, probiotic microorganisms are employed in medicaments to be administered orally in order to ameliorate or eliminate symptoms which are caused by disturbed or damaged intestinal flora. A further example are vaginal suppositories comprising microorganism cultures, for example of the *Lactobacillus acidophilus* strain, which are employed for stabilising the vaginal flora and result in a reduction in the frequency of recurrence of urinary tract infections (Reid G. et al.: Influence of three day antimicrobial therapy of *lactobacillus* vaginal suppositories on recurrence of urinary tract infections, Clin Ther 1992; 14: 11-6).

For the preparations to be effective, it is necessary that the microorganisms present therein are in living form at the time of administration and that they are capable of reproducing. The aim during the preparation of pharmaceutical administration forms comprising microorganisms and during subsequent storage thereof is therefore to maintain the activity of the microorganisms present as far as possible.

Methods for the preparation and storage of medicaments comprising microorganisms are known from the prior art. Thus, for example, EP 0 131 114 A1 describes a *Lactobacillus* preparation by application of a suspension of the bacteria to a pulverulent or granular carrier material and subsequent drying thereof. After preparation, the preparation is introduced into packaging containing an oxygen-free protective-gas atmosphere in order to maintain the activity of the microorganisms present during storage thereof.

DE 198 19 475 describes a drying method for microorganism cultures which is claimed to increase the long-term storage stability thereof. The target quantity aimed at is a water activity ($a_w$) in the material being dried of less than 0.15. In order to achieve this target quantity, the material being dried has to be dried in the fluidised-bed process and/or assistants which have an $a_w$ value of ≤0.01 must be added.

The methods known from the prior art for increasing the storage stability are unsatisfactory at least for one of the following reasons:
1. the methods are technically very complex;
2. the requirement of the water activity of the assistants is too high;
3. the storage stability of the administration forms is too low;
4. the methods are commercially too expensive;
5. the methods cause thermal damage to the microorganism cultures and/or the assistants and active compounds.

The object of the present invention was to provide a method which no longer has the described disadvantages of the prior art. In particular, the method should be simple and inexpensive to carry out, allow the use of assistants having any water activity, not result in thermal stressing of the microorganisms and the administration form comprising them and have the effect that the activity of the microorganisms is substantially retained over the entire storage time of the medicament, i.e. until it is taken by the patient.

Surprisingly, the object has been achieved by introducing a solid administration form comprising microorganisms which has been prepared in accordance with the prior art into packaging in the inner wall(s) of which an absorbent and at least one channel former is embedded over at least part of the area. The present invention therefore relates to a method for stabilising a solid pharmaceutical administration form comprising at least one microorganism culture which is characterised in that the solid pharmaceutical administration form is introduced into packaging in the inner wall(s) of which an absorbent and at least one channel former is embedded over at least part of the area. After introduction of the solid pharmaceutical administration form into the packaging, the latter is sealed, for example by means of a lid. Inner wall(s) is taken to mean the inward-facing surface of the wall(s) of the packaging, i.e. the surface(s) of the packaging which is (are) in contact with the solid pharmaceutical administration form present therein.

The method can be used for all solid pharmaceutical administration forms which are in the solid physical state at room temperature and are intended, for example, for oral, anal or vaginal administration. All solid pharmaceutical administration forms which are intended for direct administration after removal from the packaging, such as, for example, tablets, dragees, hard capsules, granules, pellets, powders, pellets, suppositories, but also those which have to be converted into the administrable form before administration, such as, for example, dried juices, for example in the form of powders which have to be converted into solution before administration, are encompassed. The pharmaceutical administration form is preferably a tablet, a dragee, a hard capsule, a granular product, a suppository, a pellet or a powder. Hard capsules have shells without added plasticiser, can be divided into an upper and lower part and consist, for example, of gelatine or starch.

Pharmaceutical administration form above and below is taken to mean a term for various technical administration forms as are known for the administration of medicaments to humans or animals. The expression pharmaceutical administration form is thus independent of a particular legal status and is in no way restricted to medicaments, ingredients which may be present are various substances, such as, for example, medicaments, food supplements and/or functional ingredients. Examples of pharmaceutical administration forms for the purposes of the present invention can be in the form of medicaments and food supplements.

Microorganisms which may be present are all microorganisms which either usually occur themselves in the healthy human or animal body or have a health-promoting action on the healthy, impaired or sick human or animal body. Microorganisms which may be present are, for example, bacteria, fungi and/or yeasts.

Preferred microorganisms are living yeasts, such as, for example, *Saccharomyces boulardii*, and/or bacteria, particularly preferably bacteria, very particularly preferably probiotic bacteria, such as, for example, lactobacilli, bifidobacteria and/or streptococci. Particular preference is given here to the species *Lactobacillus casei*, *Lactobacillus acidophilus*, *Lactobacillus reuteri*, *Lactobacillus bifidum*, *Lactobacillus gasseri*, *Lactobacillus plantarum*, *Lactobacillus johnsonii*, *Lactobacillus rhamnosus*, *Lactobacillus fermentum*, *Lactobacillus paracasei*, *Lactobacillus crispatus*, *Bifidobakterium longum*, *Bifidobakterium bifidum*, *Bifidobakterium longum*, *Bifidobacterium lactis*, *Bifidobacterium brevis*, *Bifidobacterium animalis*, *Bifidobacterium adolescentis*, *Bifidobacterium infantis*, *Streptococcus thermophilus* and/or *Lactococcus lactis*.

Suitable packaging is polymeric containers. Absorbents and channel formers may be present together either directly in the inner wall(s) of the polymer forming the container or may be applied as a layer to the inner wall(s) of the polymeric container. Absorbents and channel formers can likewise be embedded in an inlay, which is introduced into the packaging as an insert, so that at least part of the inner walls of the packaging are lined therewith.

For the purposes of the present invention, containers are both single-dose containers, such as, for example, blister packs, and also multidose containers, such as, for example, screw-lid containers or tablet tubes.

Polymers which can be employed as a mixture with absorbents and channel formers are, in particular, thermoplastics, such as, for example, polyolefins, such as polyethylene and/or polypropylenes, polyisoprenes, polybutadienes, polybutenes, polysiloxanes, polyamides, ethylene-vinyl acetate copolymers, ethylene-methacrylate copolymers, polystyrenes, polyesters, polyanhydrides, polyacrylate nitriles, polysulfonates, polyester amides, polyacrylate esters, propylene-maleic anhydride, polyethylene-maleic anhydride, polyethyleneurethanes, polyethylene-ethylvinyl alcohols, polyethylene-nylon and/or polyurethanes. The walls provided on their inner surface with absorbents and channel formers have, based on the total weight of the mixture of polymer, channel formers and absorbents, a polymer content of 10-90% by weight.

The absorbents present can basically be drying agents of any type, i.e. moisture-binding binders. Three groups of drying agents come into consideration:

The first group contains chemical substances which form hydrates with water. Examples of chemical substances of this type are anhydrous salts, which tend to absorb water or moisture and form a stable hydrate in the process. Moisture is bound and the liberation thereof is prevented by a chemical reaction.

The second group of drying agents contains substances which are reactive. The substances react with water or moisture by forming a new substance. The newly formed substances are normally stable at low temperatures, which is only reversible on expenditure of high energy. Drying agents of this type are used principally for drying solvents and as water-absorbent material in polymers which themselves have to remain in a moisture-reduced state.

The third group of drying agents binds the moisture by physical adsorption. The drying agent comprises particles having fine capillaries into which the moisture is drawn. The pore size of the capillaries and the density thereof in the drying agent determine the absorption properties here. Examples of drying agents of this type are molecular sieves, silica gels, certain synthetic polymers, such as, for example, those which are used in baby nappies, and starches. Drying agents from the third group are preferably present in the packaging since they are substantially inert and are water-insoluble. Molecular sieves having a pore size of 3 to 15 angstrom and/or silica gels having a pore size of 24 angstrom are particularly preferred here.

Channel formers which come into consideration are hydrophilic substances, such as, for example, polyglycols, ethylvinyl alcohols, glycerol, polyvinyl alcohols, polyvinylpyrrolidone, vinylpyrrolidone, N-methylpyrrolidone, polysaccharides, saccharides and/or sugar alcohols. Preferred polyglycols are polyethylene glycol and/or polypropylene glycol. Saccharides which can be used are, for example, glucose, mannose, galactose and/or fructose. Suitable sugar alcohols are, for example, mannitol, sorbitol, hexitol, dulcitol, xylitol, ribitol and/or erythrol. Polysaccharides are taken to mean, for example, dextrins and/or hydrolysed starch.

In the inner walls provided with absorbents and channel formers, the channel formers can have a proportion of 10-40% by weight, based on the total weight of the mixture of polymer, channel formers and absorbents.

Absorbents and channel formers are embedded in the inner wall(s) of the container over part of the area or over the entire area. Over part of the area means that at least part of the total area of the container forming the inner wall(s) contains absorbents and channel formers. Over the entire area means that the entire area of the container forming the inner walls contains absorbents and channel formers. According to an advantageous embodiment, absorbents and channel formers are present in at least 10%, preferably in at least 50%, particularly preferably in at least 90%, of the inner walls, based on the total inside area of the container.

Polymers which comprise absorbents and channel formers, and containers made therefrom which can be used as packaging for the method according to the invention, are known from the prior art and are described, for example, in WO 97/32663 A1, EP 1000873 A2 and WO 03/086900 A1, EP 1421991 A1, WO 00/76879 A1. Packaging which can be employed for the method of the present invention is commercially available and is offered, for example, by Capitol Specialty Plastics Inc., 2039 McMillan Street Auburn, Ala., USA, under the trade name Activ-Vial, or by Süd Chemie, Ostenrieder Str. 15, 85368 Moosburg, Germany, under the trade name 2 AP Multipolymer.

The method according to the invention enables the inexpensive provision of stable, solid pharmaceutical administration form comprising at least one microorganism culture. These can be prepared, for example, using inexpensive raw materials which cannot be used as starting material in accordance with the prior art owing to their high water activity values or have to be dried in additional steps before and/or after conversion into the pharmaceutical administration form.

Surprisingly, the method according to the invention also enables the provision of marketable products comprising solid pharmaceutical administration forms comprising at least one microorganism culture which were hitherto unsuitable for marketing in accordance with the prior art since they have inadequate storage stability. After transfer of the administration form into the packaging, water is removed continuously and over a long period from the administration form by the absorbent present in the inner wall(s) of the packaging. The removal of water takes place over a large area and under mild conditions and thus results in stabilisation of the solid pharmaceutical administration form during storage thereof.

Stabilisation of a solid pharmaceutical administration form comprising at least one microorganism culture which is comparable with the method according to the invention cannot readily be achieved even with drying after preparation, since extended drying under comparably mild conditions cannot be carried out in practice for time and cost reasons and drying at elevated temperature results in damage to the pharmaceutical administration form, in particular to the microorganism cultures present therein.

The stabilising action of the method according to the invention is based on the influence of the packaging on the solid pharmaceutical administration form, which can thus be provided in a storage-stable form. The achievement of the action according to the invention thus requires that the solid pharmaceutical administration form is present in the packaging, i.e. administration form and packaging together are in the form of a pack.

The invention therefore also relates to a pack comprising packaging in the inner wall(s) of which at least one channel former is embedded together with at least one absorbent over at least part of the area, and a solid pharmaceutical administration form comprising at least one microorganism culture, as described above and below.

The pack may contain any solid pharmaceutical administration form comprising at least one microorganism culture. According to a preferred embodiment of the invention, the pack contains, as solid pharmaceutical administration form, a solid pharmaceutical administration form intended for oral administration, in particular a tablet, a dragee, a hard capsule, a granular product, a suppository or a powder. The pharmaceutical administration form present in the pack may comprise microorganisms in any number which is necessary for the respective purpose. The solid pharmaceutical administration form present in the pack preferably comprises $10^3$ to $10^{12}$, particularly preferably $10^5$ to $10^{11}$ and very particularly preferably $10^7$ to $10^{10}$ probiotic microorganisms.

After peroral administration, probiotic microorganisms are largely deactivated during prior passage through the stomach before their health-promoting action can be achieved in the human or animal intestine. In order to ensure an adequately high activity of the probiotic microorganisms in the human and animal intestine, it is therefore preferred for the solid, oral pharmaceutical administration form present in the pack to be provided with a coating which protects the microorganisms against deactivation during passage through the stomach, but then dissolves in the intestine, so that the microorganisms are liberated there. Suitable coatings are all systems, preferably pH-controlled, such as, for example, gastric juice-resistant coatings, i.e. coatings made from materials which are insoluble in the acidic gastric juice and are soluble in the (more alkaline) intestine, or timecontrolled coatings, i.e. coatings which dissolve after a predetermined period after oral administration to the human or animal, independently of the pH of the respective environment, this period being set so that it corresponds to the duration of passage of the administration form from ingestion of the preparation to arrival thereof at the target site of the intestine. Alternatively, the microorganisms themselves instead of the entire solid pharmaceutical administration form may also be provided with the protective coating.

According to a furthermore preferred embodiment, the solid pharmaceutical administration form present in the pack, in particular if it is intended for oral administration, comprises further nutrition-relevant additives in addition to the probiotic microorganisms. Nutrition-relevant additives which may be present are preferably vitamins, mineral substances, trace elements, dietary fibre, enzymes, plant extracts, proteins, carbohydrates and/or fats. If the oral administration form comprises nutrition-relevant additives whose digestion begins as early as in the stomach, such as, for example, proteins, it is important that these nutrition-relevant additives are at least not completely enclosed by the coating.

Oral pharmaceutical administration forms which comprise probiotic microorganisms and further, nutrition-relevant additives are known from EP 931 543 A1. As described therein, formulations which comprise probiotic microorganisms together with the nutrition-relevant additives described are unstable. In order nevertheless to provide an oral administration form comprising probiotic microorganisms and nutrition-relevant additives, it is proposed that the probiotic microorganisms and the nutrition-relevant additives be distributed over layers of a multilayered tablet which are separated from one another. In order to achieve good stability, the layer comprising microorganisms should have a very low water content, which is achieved by drying the microorganism cultures and the carrier material very carefully before they are mixed. However, the requisite drying of microorganisms and carrier material and the formulation as multilayered tablet is complex in equipment terms and time-consuming and overall results in high manufacturing costs.

Surprisingly, it has been found that solid pharmaceutical administration forms comprising at least one microorganism culture and nutrition-relevant additives can be provided in a storage-stable form without microorganisms and carrier material being pre-dried and/or the microorganisms and the nutrition-relevant additives being present in layers which are in each case separated from one another by introducing the solid pharmaceutical administration form comprising the microorganisms and nutrition-relevant additives into packaging in the inner wall(s) of which at least one channel former is embedded together with at least one absorbent over at least part of the area, giving a pack comprising said packaging and the solid pharmaceutical administration form comprising microorganisms. The invention therefore also relates to a pack comprising packaging in the inner wall(s) of which at least one channel former is embedded together with at least one absorbent over at least part of the area, and a solid pharmaceutical administration form comprising at least one microorganism culture and at least one nutrition-relevant additive. The nutrition-relevant additive(s) and the microorganisms may advantageously be present in the pharmaceutical administration form present in the pack as a mixture with one another without this resulting in an unstable product. The restriction described in the prior art to formulations having a layered structure, in particular to a multilayered tablet, does not apply.

Vitamins which are preferably present in the solid pharmaceutical administration form present in the pack according to the invention are vitamin A (β-carotene), carotinoids, vitamin D, vitamin C, vitamin E, vitamins of the B complex and/or vitamin K, and related compounds thereof having comparable activity. Vitamins of the B complex which may preferably be present are folic acid, tetrahydrofolic acid and/or derivatives thereof, in particular (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid and/or 5-formimino-(6S)-tetrahydrofolic acid. The amount of vitamins generally depends on the recommended minimum required dose for the particular vitamin, although this may also be exceeded by on average 50 to 300%. Preferred ranges are between 50 and 300 mg for vitamin C, 10 to 50 mg for vitamin E, ≤1.5 mg for vitamin A and 10 μg to 20 mg for the vitamins of the B complex.

Mineral substances which are preferably present in the solid pharmaceutical administration form present in the pack according to the invention are inorganic or organic sodium, potassium, calcium, magnesium, zinc and/or iron salts which are suitable for consumption and are preferably in the form of carbonates, bicarbonates, phosphates, biphosphates, sulfates, bisulfates, chlorides, fluorides, citrates and/or lactates. The proportion of mineral substances, based on the total weight of the solid pharmaceutical administration form, is preferably from 20 to 40% by weight. The solid administration form preferably comprises silicon, chromium, manganese, iodine, molybdenum and/or selenium as trace elements.

The dietary fibre present in the solid pharmaceutical administration form present in the pack according to the invention is preferably soya bran, corn bran, wheat bran and/or whole grain, particularly preferably soya bran. The proportion of dietary fibre, based on the total weight of the solid pharmaceutical administration form, is preferably 2 to 50% by weight.

Preferred enzymes or coenzymes are lipases and/or proteases or coenzyme Q, superoxide dismutase and/or glutathione peroxidase, which promote the stomach and/or intestinal function and/or metabolism. These can be introduced in an amount known per se and in a form known per se.

The solid pharmaceutical administration form present in the pack according to the invention may in addition comprise further prebiotic substances, preferably oligofructose and/or other oligosugars.

Preferred plant extracts are dry extracts and here in particular those which comprise bioflavonoids, polyphenols, phytooestrogens and/or saponines, such as, for example, from Echinaceae.

The solid pharmaceutical administration form present in the pack according to the invention preferably comprises, as proteins, soya protein and/or dairy protein and/or, as fats, fats which comprise polyunsaturated fatty acids.

The solid pharmaceutical administration form present in the pack according to the invention may in addition, depending on the embodiment, comprise conventional assistants and additives. The choice of the assistants and/or additives also depends on the food regulations in the country in which the solid pharmaceutical administration form present in the pack is to be used. Assistants and/or additives used, for example for tablets, multilayered tablets, dragees, hard capsules, granules, pellet preparations and/or powders, are starch (for example corn starch), talc, microcrystalline cellulose, lactose, highly disperse silicon dioxide, polyvinylpyrrolidone and/or cellulose powder. Further constituents which may be present as binders and/or release agents are carbohydrates, such as, for example, mannitol, sorbitol, xylitol, glucose, sucrose, fructose, maltose, dextrose, maltodextrin and/or kaolin and/or cellulose derivatives, such as, for example, methylcellulose, hydroxypropylcellulose and/or hydroxypropylmethylcellulose, and/or calcium carbonate, calcium stearate, magnesium stearate and/or glycerol stearate. Furthermore, the solid pharmaceutical administration form present in the pack may also comprise dyes, flavours and/or aromas, as well as lubricants, antioxidants and/or stabilisers. The content of these basic substances depends on the one hand on the target content of probiotic microorganisms, vitamins, enzymes, dietary fibre, etc., and on the other hand on criteria which determine the mechanical/physical properties of the oral administration form, such as, for example, hardness, compressibility, size, colour and/or shape.

The oral administration form according to the invention can be prepared by various methods known to the person skilled in the art. These methods are known, for example, from H. Sucker, P. Fuchs, P. Speiser, "Pharmazeutische Technologie" [Pharmaceutical Technology], Stuttgart 1978 or K. H. Bauer, K. H. Frömming, C. Führer, "Pharmazeutische Technologie" [Pharmaceutical Technology], Stuttgart 1986. They are hereby incorporated by way of reference and are thus part of the disclosure.

The examples explain the invention without being restricted thereto.

EXAMPLE 1

3-Layered Tablet Analogously in EP 931 543 A1 Comprising Probiotic Bacteria

Production:

Mixtures of 3% by weight of bacterial preparation (comprising *Lactobacillus* gasseri, Bifidobacterium bifidum, Bifidobacterium longum), 10.5% by weight of inulin, 8.6% by weight of calcium phosphate, 5.7% by weight of cellulose, 2.3% by weight of assistants (disintegrants, release agents) (1st layer), mineral substances, trace elements, dyes, disintegrants, release agents, cellulose (2nd layer) and vitamins, trace elements, disintegrants, release agents and cellulose (3rd layer) (percentage data in each case based on the total tablet weight) are pressed successively in a 3-layered tablet press (rotary machine) from E. Hata to give an oblong-shaped 3-layered tablet having the dimensions 18 mm×8 mm. The tablets obtained are subsequently provided with a film coating (from aqueous solution comprising hydroxypropylmethylcellulose, hydroxypropylcellulose and a release agent), the coating was 5% by weight, based on the weight of the core, corresponding to 11 mg/cm$^2$ of tablet surface. Coated 3-layered tablets are obtained, each having a weight of 1050 mg.

Storage and Testing:

The stability of the film tablets is checked in durability studies. To this end, film tablets are either introduced into packaging in the inner wall of which a channel former is embedded together with an absorbent (packaging A) or into a polypropylene canister with screw lid (packaging B) and stored at 40° C./75% r.h. After predetermined times, the tablets are removed, and the microorganism count present in each case is determined by the Koch pour plate method by counting. The results are shown in Table 1 (average of three batches)

TABLE 1

| | | Storage condition 40° C./75% r.h. | |
|---|---|---|---|
| Test parameter | Start | 13 weeks | 26 weeks |
| | | Packaging A | |
| Probiotic cultures [KBE] | $1.4 \cdot 10^8$ | $5.9 \cdot 10^7$ | $4.6 \cdot 10^7$ |
| | | Packaging B | |
| Probiotic cultures [KBE] | $1.4 \cdot 10^8$ | $2.5 \cdot 10^3$ | $<1.0 \cdot 10^3$ |

EXAMPLE 2

Tablet Comprising Bacteria, Vitamins and Mineral Substances

Production:

A mixture of 50% by weight of sorbitol, 7.7% by weight of vitamin mixture, 24% by weight of mineral substances, 3% by weight of bacterial preparation (comprising *Lactobacillus* gasseri, Bifidobacterium bifidum, Bifidobacterium longum), 6% by weight of release agents, 4.5% by weight of dyes, 2.3% by weight of acidifiers, 2.2%% by weight of aromas and 0.06% by weight of sweeteners is pressed in a Fette E1 eccentric press to give a slightly curved, round tablet having a weight of 1000 mg and a diameter of 15 mm.

The storage and stability testing is carried out analogously to Example 1. Packaging B in this example is a polypropylene canister with screw lid and a desiccant capsule. The results are shown in Table 2.

TABLE 2

| Test parameter | Start | Storage condition 40° C./75% r.h. | |
|---|---|---|---|
| | | 13 weeks | 26 weeks |
| | | Packaging A | |
| Probiotic cultures [KBE] | $5.3 \cdot 10^7$ | $3.9 \cdot 10^7$ | $3.0 \cdot 10^7$ |
| | | Packaging B | |
| Probiotic cultures [KBE] | $5.3 \cdot 10^7$ | $5.4 \cdot 10^6$ | $<1.0 \cdot 10^3$ |

EXAMPLE 3

Granules Comprising a Bacterial Preparation

A bacterial preparation was granulated with an aqueous gelatine solution in the Glatt GPCG 3 granulator (0.5 mm nozzle) at a feed-air temperature of 65° C., an exhaust-air temperature of about 45° C. and a spray rate of 12 g/min.

EXAMPLE 4

Hard Gelatine Capsule Containing a Bacterial Preparation

A mixture of 98% of bacterial preparation, 1% of ascorbic acid and 1% of inulin was introduced into hard gelatine capsules (size 0).

EXAMPLE 5

Hard Gelatine Capsule Containing a Bacterial Preparation

A mixture at least comprising a bacterial preparation (comprising *Lactobacillus casei, Lactococcus lactis, Lactobacillus acidophilus, Bifidobacterium bifidum*) was introduced into hard gelatine capsules (size 0).

The storage and stability testing is carried out analogously to Example 1. Packaging B in this example is an organic polymer/aluminium blister pack. The results are shown in Table 3.

TABLE 3

| Test parameter | Start | Storage condition 40° C./75% r.h. | |
|---|---|---|---|
| | | 13 weeks | 26 weeks |
| | | Packaging A | |
| Probiotic cultures [KBE] | $1.1 \cdot 10^{10}$ | $2.8 \cdot 10^9$ | $1.6 \cdot 10^9$ |
| | | Packaging B | |
| Probiotic cultures [KBE] | $1.1 \cdot 10^{10}$ | — | $<1.0 \cdot 10^3$ |

EXAMPLE 6

Hard Gelatine Capsule Containing a Bacterial Preparation

A mixture of a bacterial preparation (comprising *Lactobacillus* GG), microcrystalline cellulose and magnesium stearate was introduced into hard gelatine capsules (size 0).

The storage and stability testing is carried out analogously to Example 1. The results are shown in Table 4.

TABLE 4

| Test parameter | Start | Storage condition 40° C./75% r.h. | |
|---|---|---|---|
| | | 13 weeks | 26 weeks |
| | | Packaging A | |
| Probiotic cultures [KBE] | $2.4 \cdot 10^{10}$ | $1.2 \cdot 10^8$ | $8.7 \cdot 10^7$ |

EXAMPLE 7

Powder Comprising a Bacterial Preparation

The packaged powder comprises a bacterial preparation (comprising *Lactobacillus* GG), maltodextrin, sorbitol and sucrose.

The storage and stability testing is carried out analogously to Example 1. The results are shown in Table 5.

TABLE 5

| Test parameter | Start | Storage condition 40° C./75% r.h. | |
|---|---|---|---|
| | | 13 weeks | 26 weeks |
| | | Packaging A | |
| Probiotic cultures [KBE] | $5.7 \cdot 10^9$ | $4.3 \cdot 10^8$ | $1.3 \cdot 10^9$ |

The invention claimed is:

1. A method for stabilising a solid pharmaceutical administration form comprising at least one living microorganism culture, said method comprising introducing said solid pharmaceutical administration form into packaging in the inner wall(s) of which at least one channel former is embedded together with at least one absorbent over at least part of the area.

2. A method according to claim 1, wherein said solid pharmaceutical administration form is a tablet, a dragee, a capsule, a granular product, a suppository, a pellet or a powder.

3. A method according to claim 1, wherein said microorganism culture present is probiotic microorganisms.

4. A method according to claim 3, wherein said probiotic microorganisms are lactobacilli, bifidobacteria, or streptococci, *Lactobacillus casei, Lactobacillus acidophilus, Lactobacillus reuteri, Lactobacillus bifidum, Lactobacillus gasseri, Lactobacillus plantarum, Lactobacillus johnsonii, Lactobacillus rhamnosus, Lactobacillus fermentum, Lactobacillus paracasei, Lactobacillus crispatus, Bifidobakterium longum, Bifidobakterium bifidum, Bifidobakterium longum, Bifidobacterium lactis, Bifidobacterium brevis, Bifidobacterium animalis, Bifidobacterium adolescentis, Bifidobacterium infantis, Streptococcus thermophilus* and/or *Lactococcus lactis*.

5. A method according to claim 1, wherein said packaging comprises, as absorbent, a drying agent which binds moisture by physical adsorption.

6. A method according to claim 5, wherein said drying agent is a molecular sieve or silica gel.

7. A pack comprising packaging having inner walls, having at least one channel former embedded together with at least one absorbent over at least part of the area and a solid pharmaceutical administration form comprising at least one microorganism culture within said packaging.

8. A pack according to claim 7, wherein said solid pharmaceutical administration form present in the packaging is a form suitable for oral administration.

9. A pack according to claim 7, wherein said solid pharmaceutical administration form present in the packaging comprises $10^3$ to $10^{12}$ microorganisms.

10. A pack according to claim 7, wherein said pharmaceutical administration form present in the packaging comprises further nutrition-relevant additives.

11. A pack according to claim 9, wherein said solid pharmaceutical administration form present in the packaging comprises $10^5$ to $10^{11}$ microorganisms.

12. A pack according to claim 9, wherein said solid pharmaceutical administration form present in the packaging comprises $10^7$ to $10^{10}$ microorganisms.

13. A pack according to claim 10, wherein said further nutrition-relevant additives are selected from vitamins, mineral substances, trace elements, dietary fiber, enzymes, plant extracts, proteins, carbohydrates, and/or fats.

14. A pack according to claim 7, wherein said solid pharmaceutical administration form is a tablet, a dragee, a capsule, a granular product, a suppository, a pellet or a powder.

15. A pack according to claim 7, wherein said microorganism culture present is probiotic microorganisms.

16. A pack according to claim 15, wherein said probiotic microorganisms are lactobacilli, bifidobacteria, or streptococci, *Lactobacillus casei, Lactobacillus acidophilus, Lactobacillus reuteri, Lactobacillus bifidum, Lactobacillus gasseri, Lactobacillus plantarum, Lactobacillus johnsonii, Lactobacillus rhamnosus, Lactobacillus fermentum, Lactobacillus paracasei, Lactobacillus crispatus, Bifidobakterium longum, Bifidobakterium bifidum, Bifidobakterium longum, Bifidobacterium lactis, Bifidobacterium brevis, Bifidobacterium animalis, Bifidobacterium adolescentis, Bifidobacterium infantis, Streptococcus thermophilus* and/or *Lactococcus lactis*.

* * * * *